United States Patent
Tomihata et al.

(10) Patent No.: US 6,616,687 B1
(45) Date of Patent: Sep. 9, 2003

(54) SURGICAL SUTURE

(75) Inventors: Kenji Tomihata, Ayabe (JP); Masakazu Suzuki, Ayabe (JP); Ikuo Sasaki, Ayabe (JP)

(73) Assignee: Gunze Limited, Kyoto (JP)

( * ) Notice: Subject to any disclaimer, the term of this patent is extended or adjusted under 35 U.S.C. 154(b) by 0 days.

(21) Appl. No.: 09/830,509

(22) PCT Filed: Oct. 28, 1999

(86) PCT No.: PCT/JP99/05961

§ 371 (c)(1),
(2), (4) Date: Apr. 26, 2001

(87) PCT Pub. No.: WO00/25837

PCT Pub. Date: May 11, 2000

(30) Foreign Application Priority Data

Oct. 30, 1998 (JP) ............................................ 10-309792

(51) Int. Cl.$^7$ .............................................. A61B 17/04
(52) U.S. Cl. ....................................... 606/228; 606/230
(58) Field of Search ................................ 606/228–231; 527/200; 528/354; 525/468, 411, 413, 415, 461

(56) References Cited

U.S. PATENT DOCUMENTS

| | | |
|---|---|---|
| 4,027,676 A | 6/1977 | Mattei |
| 4,057,537 A | 11/1977 | Sinclair |
| 4,201,216 A | 5/1980 | Mattei |
| 4,532,929 A | 8/1985 | Mattei et al. |
| 4,605,730 A | 8/1986 | Shalaby et al. |
| 4,624,256 A | 11/1986 | Messier et al. |
| 4,700,704 A | 10/1987 | Jamiolkowski et al. |
| 4,788,979 A | 12/1988 | Jarrett et al. |
| 4,844,067 A | 7/1989 | Ikada et al. |
| 5,304,205 A | * 4/1994 | Shinoda et al. ............. 606/230 |
| 5,378,540 A | 1/1995 | Olson |
| 5,380,780 A | 1/1995 | Olson |
| 5,609,609 A | 3/1997 | Ohshima et al. |
| 5,747,637 A | 5/1998 | Shinoda et al. |
| 5,786,022 A | 7/1998 | Agarwal et al. |
| 5,797,962 A | * 8/1998 | Tomihata et al. ........... 606/228 |

FOREIGN PATENT DOCUMENTS

| | | |
|---|---|---|
| EP | 0 261 470 | 3/1988 |
| JP | 64-056055 | 3/1989 |
| JP | 09-059356 | 3/1997 |
| WO | WO 92/04393 | 3/1992 |

* cited by examiner

*Primary Examiner*—Gloria M. Hale
(74) *Attorney, Agent, or Firm*—Knobbe, Martens, Olson & Bear LLP

(57) ABSTRACT

The present invention relates to a coating material for surgical sutures which comprises as essential ingredients a copolymer having repeating units of lactic acid and ε-caprolacton and calcium stearate; and a surgical suture comprising a lactic acid/ε-caprolacton copoymer in which a lactide/ε-caprolacton ratio is (70–85 mol %)/(30–15 mol %) and the number of ε-caprolacton repeating unit is 2.5 or greater on the average.

13 Claims, No Drawings

SURGICAL SUTURE

TECHNICAL FIELD

The present invention relates to surgical sutures and, more specifically, to coating materials for surgical sutures and to absorbable sutures having a coating.

BACKGROUND ART

The surgical suture is one of the medical devices used for a long time. In recent years, absorbable sutures which obviate the need of the removal of the suture after surgery have been increasingly produced by using absorbable materials. Although sutures comprising mainly polyglycolic acid were developed, the threads were so rigid that the suture was produced in the form of a multifilament consisting of a number of filaments.

However, a multifilament had problems of, for example, requiring a complicated production process, having poor slip properties due to its surface roughness during manipulation, occasionally causing tissue injuries during suturing procedures, and entailing a risk of infection due to capillary properties.

In order to solve those problems, various methods have been proposed to apply a coating onto the surface of multifilament sutures, as disclosed in Japanese Unexamined Patent Publication No. 229111/1996.

On the other hand, a monofilament provides advantages that the production process can be simplified, that the suture does not cause tissue injuries during suturing procedures due to its smooth surface, and that the risk of infection may be considerably reduced due to no capillary properties.

Products of absorbable monofilament surgical sutures have been commercially available so far, using as raw materials a copolymer of glycolic acid and caprolacton, a copolymer of glycolic acid and trimethylene carbonate or polydioxanone.

However, monofilament sutures have shortcomings of poor handling characteristics due to rigidity and difficulty in suture and knot. Additionally, monofilament sutures have the shortcoming of requiring formation of knots many times, since a tied knot is likely to loosen.

In order to overcome those shortcomings, a absorbable monofilament suture composed of a lactic acid/caprolacton copolymer was designed, as disclosed in Japanese Unexamined Patent Publication No.317968/1996. This material had moderate softness, flexibility and formability to allow formation of smaller knots and further made it possible to reduce the number of tying knots owing to good knot security.

Although a sufficient handling characteristics was achieved as set forth above, the absorbable monofilament surgical suture made of a lactic acid/caprolacton copolymer had difficulty in enhancing tenacity of the strand due to the nature of the material.

In order to overcome those shortcomings of monofilament sutures, the method for coating the suture with, for example, silicone oil has been commonly performed to impart lubricity on the surface of suture.

However, in case the material of the suture is degradable and absorbable in the living body, it is not preferable to apply coating of materials which are not degradable, absorbable or excretory in the living body.

It is an object of the present invention to improve tenacity of the suture composed of a lactic acid/caprolacton copolymer while retaining flexibility of the suture.

It is another object of the present invention to provide a coating composition which exhibits a good affinity for the suture body and synergistically improves knot strength, and to provide a suture which has such a coating.

DISCLOSURE OF THE INVENTION

The present invention relates to a method for applying coating onto surgical sutures.

1. A coating material to be applied onto the surface of a suture, comprising a $\epsilon$-caprolacton homopolymer or a copolymer of $\epsilon$-caprolacton and another absorbable monomer, and calcium stearate.

2. The coating material as defined in Item 1 in which said another absorbable monomer is lactide.

3. The coating material as defined in Item 1 in which a percentage composition of a copolymer of $\epsilon$-caprolacton and lactide is 88–97:12–3% in molar ratio and a blending ratio of calcium stearate is 0.01 to 1.5 wt. %.

4. The coating material as defined in Item 1 in which a percentage composition of a copolymer of $\epsilon$-caprolacton and lactide is 70–80:30–20% in molar ratio and a blending ratio of calcium stearate is 0.1 to 2.5 wt. %.

5. The coating material as defined in Item 1 in which a percentage composition of a copolymer of $\epsilon$-caprolacton and lactide is 45–55:55–45% in molar ratio and a blending ratio of calcium stearate is 1.0–3.0 wt. %.

6. The coating material as defined in Item 1 comprising a homopolymer of $\epsilon$-caprolacton and calcium stearate whose blending ratio is 0.01 to 1.0 wt. %.

7. An absorbable suture coated with the coating material as defined in any of Items 1–6.

8. The suture as defined in Item 7 in which the absorbable suture is a monofilament suture.

9. The suture as defined in Item 8 which is a copolymer of $\epsilon$-caprolacton and lactide.

10. The suture as defined in Item 9 in which a percentage composition of a copolymer of $\epsilon$-caprolacton and lactide in the absorbable suture is 15–30:85–70% in molar ratio.

11. The suture as defined in Item 10 in which the average number of continuous $\epsilon$-caprolacton repeating unit is 2.5 or more.

12. The suture as defined in Item 10 in which a percentage composition of a copolymer of $\epsilon$-caprolacton and lactide in the absorbable suture is 20–30 80–70% in molar ratio.

13. The suture as defined in Item 7 in which a knot pull strength has been improved by 10 to 50% by coating.

14. A surgical suture comprising a copolymer of lactic acid and $\epsilon$-caprolacton in which lactide:$\epsilon$-caprolacton is 70–85:30–15 mole % and the average number of continuous $\epsilon$-caprolacton repeating unit is 2.5 or more.

15. The surgical suture as defined in Item 14 in which the suture is a monofilament.

(1) Sutures having a coating

The coating material to be applied onto the absorbable monofilament surgical suture according to the present invention comprises as an essential ingredient $\epsilon$-caprolacton, which may be a homopolymer of $\epsilon$-caprolacton or a copolymer of $\epsilon$-caprolacton and another absorbable monomer or monomers. Examples of another absorbable monomer include lactide, glycolide, trimethylene carbonate, dioxanone and the like, among which lactide is specifically mentioned.

A preferred copolymer is a copolymer of $\epsilon$-caprolacton and lactic acid, such as lactide as a repeating unit. The copolymer having a repeating unit of ε-caprolacton and lactic acid such as lactide may further comprise an additional biodegradable and bioabsorbable repeating unit in an amount not causing considerable adverse effects. As such an additional repeating unit, for example, glycolic acid, trimethylene carbonate, dioxanone are exemplified.

It is preferable that the coating material to be applied onto the absorbable monofilament surgical suture according to the present invention comprises an ε-caprolacton monomer alone or a copolymer which consists of lactic acid and ε-caprolacton as a repeating unit. However, the coating composition according to the present invention may comprise an additional biodegradable and absorbable polymer in an amount not causing adverse effects to the physical properties as the coating material. Examples of such polymers include polyglycolic acid, trimethylene carbonate and polydioxanone.

The coating material to be applied onto the absorbable monofilament surgical suture according to the present invention can serve as a coating material even when the material comprises an ε-caprolacton monomer alone or a copolymer alone which consists of lactic acid and ε-caprolacton as the repeating unit. However, if it is desired to further improve handling properties during manipulation, calcium stearate, that is a commonly used additive, is preferably used in combination.

When a proportion of ε-caprolacton and lactic acid employed in the copolymer is expressed as mole % of ε-caprolacton and lactide, that is a dimer of lactic acid, preferable ratios of ε-caprolacton:lactide is 88–97:12–3 mole %, or 70–80:30–20 mole %, or 45–55:55–45 mole %.

Lactic acids may be any of L-lactic acid, D-lactic acid and D,L-lactic acid (racemate), but L-lactic acid is preferably used.

The absorbable monofilament surgical suture which is coated with the coating material of the invention may be made of any material such as, for example, a copolymer of ε-caprolacton and glycolic acid, polydioxanone, a glycolic acid/trimethylene carbonate/lactic acid copolymer, a glycolic acid/trimethylene carbonate/dioxanone copolymer, and the like. In view of compatibility with the coating material, a lactic acid/ε-caprolacton copolymer is preferable. More preferably, lactide:ε-caprolacton=70–85:30–15 mol %, and particularly preferably lactide:ε-caprolacton=70–80: 30–20 mol %. The applicable size of the suture can range from USP 2 to 10–0.

It is possible to coat the absorbable monofilament surgical suture with an ε-caprolacton unit alone or a copolymer alone which consists of lactic acid and ε-caprolacton as a repeating unit. However, if improved handling properties during a surgical procedure as well as enhanced breaking strength represented by knot tenacity which is measured according to the USP Codex are desired, it is necessary to simultaneously use a higher fatty acid salt such as calcium stearate. The optimum amounts of calcium stearate used may vary depending on the polymers employed.

The optimum amounts of calcium stearate added are defined as follows. When the biodegradable and bioabsorbable polymer employed in the coating material is a homopolymer of ε-caprolacton, the optimum amount of calcium stearate is 0.01–1.0 wt. %. In the case of ε-caprolacton:lactide=88–97:12–3 mol %, the optimum amount of calcium stearate is 0.01–1.5 wt. %, in the case of ε-caprolacton:lactide=70–80:30–20 mol %, the optimum amount is 0.1–2.5 wt. %, and in the case of ε-caprolacton: lactide=45–55:55–45 molt, the optimum amount is 1.0–3.0 wt. %. The optimum amounts may vary in relation to the concentration of the polymers employed in the coating material.

Specifically, the coating method begins with thorough dissolution of the polymer in a solvent. The solvent employed may be any commonly used organic solvent. Preferably, acetone is used since aceton does not considerably dissolve the suture body. Through this dissolution, the coating material becomes more adhesive to the suture body and the incidence of peeling of coatings decreases.

In case a higher fatty acid salt such as calcium stearate is simultaneously used, this salt is added in a predetermined amount to the solution described above which contains the polymer. The higher fatty acid salt is slightly soluble in solvents of various kinds, and therefore, the higher fatty acid salt is used in the form of a dispersion. For the purpose of uniform coating, it is preferred to maintain stirring of the coating solution continuously throughout coating procedures.

Knot-pull strength improvement introduced by applying coating is preferably 10 to 50%, more preferably at least 20%.

(2) Surgical sutures

The surgical suture according to the present invention is a copolymer consisting of lactic acid and ε-caprolacton as a repeating unit. When the proportion is expressed by the molar ratio of lactide, that is a dimer of lactic acid, to ε-caprolacton, lactide:ε-caprolacton=70–85:30–15 mol %, preferable 72.5–77.5:27.5–22.5. In case the proportion of ε-caprolacton is too high, the resultant copolymer has a problem in stability such as causing shrinkage at the time of thermosetting and sterilization treatment. In the case of lactide:ε-caprolacton=50:50 mol %, the resultant copolymer, although rapidly degradable and satisfactorily flexible, does not meet the requirements of the suture owing to its rubber-like nature. From the foregoing, the above-stated ratios are adopted for polymerization.

Lactic acids (lactides) may be any of L-lactic acid (L-lactide), D-lactic acid (D-lactide), DL-lactic acid (racemic modification) (DL-lactide). L-lactic acid (L-lactide) is preferably used.

The surgical suture according to the present invention can achieve enhanced tenacity when the length of one repeating unit of the two components becomes longer. In more detail, the average number of continuous ε-caprolacton determined by 1H-NMR is preferably 2.5 or greater, more preferably 2.7 or greater, most preferably about 2.8–4.

Too small average number of the continuous repeating unit results in lower tenacity of the suture, while too large average number of continuous repeating unit results in too rigid sutures. The upper limit of the average number of continuous chain unit is not limited insofar as the portion like a block copolymer, in which ε-caprolacton alone has been polymerized, is not contained in the polymer. However, the limit is preferably about 10 or less, more preferably about 6 or less, most preferably about 4 or less.

The weight average molecular weight of the copolymer according to the present invention preferably ranges from 100,000 to 1,000,000.

The suture produced by using a copolymer in which the average number of continuous ε-caprolacton is 2.5 or greater can not only achieve enhanced strength over the suture obtained using a copolymer with a shorter repeating unit, but also provide inproved knot breaking strength enough to meet the requirements of the suture as measured according to the USP.

The sutures according to the present invention may be a monofilament strand or a multifilament strand, preferably a monofilament strand.

In order to elongate the length of the specific repeating unit of the copolymer according to the present invention, a bulk polymerization method is preferably carried out, as typically disclosed in Japanese Unexamined Patent Publication No.501045/1994. The publication sets forth that there is a tendency that the average number of continuous repeating unit of each constitutional component generally becomes longer when polymerization is conducted at a lower temperature for a longer period of time. The copolymers having a longer average length of the continuous constituent, suitable enough for use as the raw material according to the present invention, can be produced if polymerization is carried out at a lower temperature and for a longer period of time. Thus, it is possible for the copolymer, even within a common category of a random copolymer, not only to satisfy the physical properties required as fibers, specifically as medical sutures, such as tenacity (in pulling and knotting), but also to exhibit flexibility needed for use as the suture when the average length of the continuous component is lengthened. Polymerization temperature is usually at about 70° C. to 160° C., preferably at about 110° C. to 150° C.

Although Japanese Unexamined Patent Publication No.59356/1997 discloses an A-B or A-B-A block copolymer produced by polymerizing caprolacton followed by polymerizing another constituent (lactide), the block copolymer is not preferable for use as a suture since the block copolymer achieves high pulling tenacity but provides rather low flexibility.

BEST MODE FOR CARRYING OUT THE INVENTION

The present invention will now be illustrated by the following Examples, but it is to be understood that the invention is not limited to the Examples.

EXAMPLE 1A

Using a copolymer of L-lactic acid and ε-caprolacton (lactide/ε-caprolacton=25/75 mol %) together with calcium stearate (CaSt.), a coating material was applied to the copolymer.

(1) Solvent acetone (2) Concentration of copolymer (polymer) 2 W/V %

(3) Concentration of calcium stearate 0.2 and 2 W/V %

The above three ingredients were mixed and a strand was passed through the mixture to apply coating thereto at the rate of about 10 m/min, with continuously stirring the mixture. The strand used was a monofilament having a lactide/ε-caprolacton ratio of 75/25 mol % and corresponding to the USP size 0.

Knot-pull strength of the coated strand was measured according to the USP established to assess Knot-pull strength of the suture. Knot breaking extension was the value of extension measured at break. Knot-pull strength of the strand prior to applying coating was measured for reference. The results are shown in Table 1 below.

TABLE 1

|  | Knot-pull strength (g) | Knot Breaking Elongation (%) | Knot-pull strength Improvement (%) |
| --- | --- | --- | --- |
| Before Coating | 4025 | 29.4 |  |
| 2% polymer, 0.2% CaSt. | 5067 | 40.6 | 25.9 |

TABLE 1-continued

|  | Knot-pull strength (g) | Knot Breaking Elongation (%) | Knot-pull strength Improvement (%) |
| --- | --- | --- | --- |
| 2% polymer, 2% CaSt. | 4676 | 40.5 | 16.1 |

Knot-pull strength improvement was calculated by dividing the value of improved strength by the value of the strength measured prior to applying coating, followed by multiplied by 100.

EXAMPLE 2A

Using a copolymer of L-lactic acid and ε-caprolacton (lactide/ε-caprolacton=50/50 mol %) together with calcium stearate, a coating material was applied to the copolymer.

(1) Solvent acetone (2) Concentration of copolymer 2 W/V %

(3) Concentration of calcium stearate 0.2 and 2 W/V %

The above three ingredients were mixed and the strand, which was the same one as used in Example 1, was passed through the mixture at the rate of about 10 m/min *to apply coating thereto, with continuously stirring the mixture. The suture used was a monofilament having a lactide/ε-caprolacton ratio of 75/25 mol % and corresponding to the USP size 0.

Knot-pull strength of the coated strand was measured according to the USP established to assess strength of the suture. Knot-pull strength of the strand prior to applying coating was measured for reference. The results are shown in Table 2 below.

TABLE 2

|  | Knot-pull strength (g) | Knot Breaking Elongation (%) | Knot-pull strength Improvement (%) |
| --- | --- | --- | --- |
| Before Coating | 4025 | 29.4 |  |
| 2% polymer, 0.2% CaSt. | 4086 | 32.7 | 1.5 |
| 2% polymer, 2% CaSt. | 5023 | 42.3 | 24.8 |

EXAMPLE 3A

Using a copolymer of L-lactic acid and ε-caprolacton (lactide/ε-caprolacton=8/92 mol %) together with calcium stearate, a coating material was applied to the copolymer.

(1) Solvent acetone (2) Concentration of copolymer 2 W/V %

(3) Concentration of calcium stearate 0, 0.1, 0.2, 0.5, 1 and 2 W/V %

The above three ingredients were mixed and the strand, which was the same one as used in Example 1, was passed through the mixture at the rate of about 10 m/min to apply coating thereto, with continuously stirring the mixture. The strand used was a monofilament having a lactide/ε-caprolacton ratio of 75/25 mol % and corresponding to the USP size 2–0.

Knot-pull strength of the coated suture was measured according to the USP which is established to assess strength of the suture. Knot-pull strength of the strand prior to applying coating was measured for reference. The results are shown in Table 3 below.

TABLE 3

|  | Knot-pull strength(g) | Knot Breaking Elongation (%) | Knot-pull strength Improvement (%) |
| --- | --- | --- | --- |
| Before Coating | 2219 | 30.6 |  |
| 2% polymer, 0% CaSt. | 2432 | 33.7 | 9.6 |
| 2% polymer, 0.1% CaSt. | 2937 | 39.4 | 32.4 |
| 2% polymer, 0.2% CaSt. | 2640 | 39.6 | 20.0 |
| 2% polymer, 0.5% CaSt. | 2597 | 41.1 | 17.0 |
| 2% polymer, 1% CaSt. | 2625 | 41.3 | 18.3 |
| 2% polymer, 2% CaSt. | 2372 | 35.0 | 6.9 |

EXAMPLE 4A

Using an $\epsilon$-caprolacton polymer together with calcium stearate, a coating material was applied thereto.

(1) Solvent acetone (2) Concentration of an $\epsilon$-caprolacton polymer 0.1, 0.5, 1.0 W/V %

(3) Concentration of calcium stearate 0.1 W/V %

The above three ingredients were mixed and the strand, which was the same one as used in Example 1, was passed through the mixture at the rate of about 10 m/min to apply coating thereto, with continuously stirring the mixture. The strand used was a monofilament having a lactide/$\epsilon$-caprolacton ratio of 75/25 mol % and corresponding to the USP size 0.

Knot-pull strength of the coated strand was measured according to the USP established to assess strength of the suture. Knot-pull strength of the strand prior to applying coating was measured for reference. The results are shown in Table 4 below.

TABLE 4

|  | Knot-pull strength (g) | Knot Breaking Elongation (%) | Knot-pull strength Improvement (%) |
| --- | --- | --- | --- |
| Before Coating | 3799 | 28.2 |  |
| 0.1% polymer, | 3815 | 24.9 | 0.4 |
| 0.1% polymer, 0.1% CaSt. | 4855 | 34.9 | 27.8 |
| 0.5% polymer, 0.1% CaSt. | 5284 | 40.3 | 39.1 |
| 1.0% polymer, 0.1% CaSt. | 5000 | 39.6 | 31.6 |

EXAMPLE 1B

Monofilament strands were produced according to the method disclosed in Japanese Unexamined Patent Publication No.317968/1996, using a copolymer of lactic acid and $\epsilon$-caprolacton having a variety of the average number of continuous $\epsilon$-caprolacton repeating unit (hereinafter referred to simply as Lc), analyzed by the method of Gebriele Perego et al (Biomaterials, Vol.15, 189 (1994)) and the method of Hans R. Kricheldorf et al (J. Macromol. Sci. -Chem., Vol.A24, 1345 (1987)) using $^1$H-NMR spectra. The resultant monofilament strands were subjected to tests.

Two kinds of polymers, No.1 (Lc=2.95) and No.2 (Lc=2.23), were employed and strands having an average diameter of 0.5 mm were prepared. Those strands were evaluated for tensile strength at a chuck distance of 100 mm and a pulling rate of 100 mm/min. The results are shown in Table 5 below.

TABLE 5

|  | Strength (g) | Strength (g/d) | Lc |
| --- | --- | --- | --- |
| No. 1 | 8746 | 4.00 | 2.95 |
| No. 2 | 7059 | 3.23 | 2.23 |

EXAMPLE 2B

Monofilament strands were produced according to the method disclosed in Japanese Unexamined Patent Publication No.317968/1996, using a copolymer of lactic acid and $\epsilon$-caprolacton having a variety of the average number of continuous $\epsilon$-caprolacton repeating unit (hereinafter referred to simply as Lc), analyzed by the method of Gebriele Perego et al (Biomaterials, Vol.15, 189 (1994)) and the method of Hans R. Kricheldorf et al (J. Macromol. Sci. -Chem., Vol.A24, 1345 (1987)) using $^1$H-NMR spectra. The resultant monofilament strands were subjected to tests.

Two kinds of polymers, No.1 (Lc=3.36) and No.2 (Lc=1.93), were employed and the strands having an average diameter of 0.315 mm were obtained. Those strands were evaluated for tensile strength at a chuck distance of 100 mm and a pulling rate of 100 mm/min. The results are shown in Table 6 below.

TABLE 6

|  | Strength (g) | Strength (g/d) | Lc |
| --- | --- | --- | --- |
| No. 3 | 3240 | 3.75 | 3.36 |
| No. 4 | 2838 | 3.36 | 1.93 |

Specific conditions (which are the same as in Examples 1 and 2) to produce the monofilament strands were illustrated as follows.

Step 1. melt spinning and primary drawing: drawing nine-fold in a water-bath at a spinning temperature and a water-bath temperature shown in Table 3;

Step 2. secondary drawing (re-drawing): 120 to 130° C., drawing 1.67-fold;

Step 3. heat treatment (thermosetting): 120° C., 60 min while the copolymer was wound around a bobbin with moderate tension; and Step 4. shrinkage treatment: 60° C., 15 hours.

Monofilament strands Nos.1 to 4, produced under the conditions described above, are characterized by the following lactide(LA)/$\epsilon$-caprolacton(CL) ratios (mol %), Lc, spinning temperature and water-bath temperature shown in Table 7.

TABLE 7

| No | LA:CL (mol %) | Lc | Spinning Temperature (° C.) | Water-Bath Temperature (° C.) |
| --- | --- | --- | --- | --- |
| 1 | 75.5:24.5 | 2.95 | 235 | 86 |
| 2 | 76.9:23.1 | 2.23 | 224 | 80 |

TABLE 7-continued

| No | LA:CL (mol %) | Lc | Spinning Temperature (° C.) | Water-Bath Temperature (° C.) |
|---|---|---|---|---|
| 3 | 75.3:24.7 | 3.36 | 243 | 82 |
| 4 | 74.6:25.4 | 1.93 | 217 | 76 |

According to the method of the present invention to apply coating, absorbable monofilament surgical sutures achieve improvement in slip properties on their surface and handling properties during use. These improvements may prevent break of strands caused by excess force applied during manipulation due to poor slip properties in spite of sufficient tenacity. Furthermore, in comparison with uncoated sutures, the coated sutures achieve improvement in knot-pull strength by 10 to 50% as measured according to the USP Codex.

According to the present invention, absorbable surgical sutures can be provided which are flexible, easy to tie knots and unlikely to render the tied knots loosen, and furthermore have high knot-pull strength.

What is claimed is:

1. A coating material adapted to be applied onto a surface of a suture, comprising a copolymer of $\epsilon$-caprolacton and lactide, and calcium stearate, wherein a percentage composition of said copolymer of $\epsilon$-caprolacton and lactide is 88–97:12–3% in molar ratio and a blending ratio of said calcium stearate is 0.01 to 1.5 wt. %.

2. A coating material adapted to be applied onto a surface of a suture, comprising a copolymer of $\epsilon$-caprolacton and lactide, and calcium stearate, wherein a percentage composition of said copolymer of $\epsilon$-caprolacton and lactide is 70–80:30–20% in molar ratio and a blending ratio of said calcium stearate is 0.1 to 2.5 wt. %.

3. A coating material adapted to be applied onto a surface of a suture, comprising a copolymer of $\epsilon$-caprolacton and lactide, and calcium stearate, wherein a percentage composition of said copolymer of $\epsilon$-caprolacton and lactide is 45–55:55–45% in molar ratio and a blending ratio of said calcium stearate is 1.0–3.0 wt. %.

4. A coating material adapted to be applied onto a surface of a suture, comprising a homopolymer of $\epsilon$-caprolacton and calcium stearate, wherein a blending ratio of said calcium stearate is 0.01 to 1.0 wt. %.

5. An absorbable suture coated with the coating material as defined in any of claims 1–4.

6. The suture as defined in claim 5 in which the absorbable suture is a monofilament suture.

7. The suture as defined in claim 6 which is a copolymer of $\epsilon$-caprolacton and lactide.

8. The suture as defined in claim 7 in which a percentage composition of a copolymer of $\epsilon$-caprolacton and lactide in the absorbable suture is 15–30:85–70% in molar ratio.

9. The suture as defined in claim 8 in which the average number of continuous $\epsilon$-caprolacton repeating unit is 2.5 or more.

10. The suture as defined in claim 8 in which a percentage composition of a copolymer of $\epsilon$-caprolacton and lactide in the absorbable suture is 20–30:80–70% in molar ratio.

11. The suture as defined in claim 5 in which a knot pull strength has been improved by 10 to 50% by coating.

12. A surgical suture comprising a copolymer of lactic acid and $\epsilon$-caprolacton in which lactide: $\epsilon$-caprolacton is 70–85:30–15 mole % and the average number of continuous $\epsilon$-caprolacton repeating unit is 2.5 or more.

13. The surgical suture as defined in claim 12 in which the suture is a monofilament.

* * * * *